United States Patent [19]
Peterson

[11] Patent Number: 6,067,864
[45] Date of Patent: May 30, 2000

[54] MULTIPORT VALVE SYSTEM THROUGH WHICH SAMPLE GAS CONTINUOUSLY FLOWS IN SELECTED AND NON SELECTED PORTS

[76] Inventor: Roger Peterson, Drawer 567, County Rd. 375, Old Ocean, Tex. 77463

[21] Appl. No.: 08/977,797

[22] Filed: Nov. 25, 1997

[51] Int. Cl.[7] .................................................. F16K 11/06
[52] U.S. Cl. .................... 73/863.33; 137/625.18
[58] Field of Search ................................ 73/23.41, 23.42, 73/863.31, 863.33; 137/625.18, 625.46

[56] References Cited

U.S. PATENT DOCUMENTS

| | | | |
|---|---|---|---|
| 3,765,247 | 10/1973 | Riggs | 73/806.33 X |
| 4,156,437 | 5/1979 | Chivens et al. | 137/554 |
| 4,601,211 | 7/1986 | Whistler | 73/863.33 |

*Primary Examiner*—John Fox
*Attorney, Agent, or Firm*—Gunn & Associates, P.C.

[57] ABSTRACT

A multiport valve system is disclosed in which sample gas continuously flows through all ports. More specifically, gas flowing to a specific port is selected for analysis, and gas continuously flows through the valve at this port during the analysis. In addition, non selected gas samples, which are defined as gas samples not currently being analyzed, continuously flow through non selected ports thereby always providing fresh samples at these ports when they subsequently become selected ports for analysis. Non selected gas is purged from the valve as waste. A positive pressure is maintain between portions of the valve containing selected gas and portions of the valve containing non selected gas to prevent contamination of the selected gas.

21 Claims, 2 Drawing Sheets

MULTIPORT VALVE SYSTEM THROUGH WHICH SAMPLE GAS CONTINUOUSLY FLOWS IN SELECTED AND NON SELECTED PORTS

BACKGROUND OF THE INVENTION

This disclosure is directed toward a multiport valve system, and more particularly directed toward a multiport valve system in which sample gas continuously flows through all ports, including ports from which gas samples are not currently being analyzed.

BACKGROUND OF THE ART

Toxic and explosive gases are a growing hazard to both life and property in an industrialized society. Industrial manufacturing and processing facilities can be especially prone to emit such gases. As an example, a petrochemical manufacturing plant typically uses toxic and explosive gas products in the manufacturing process, and produces other equally hazardous gases as waste products. Such facilities utilize hundreds of valves and thousands of yards of piping to transport and control the flow of raw materials and manufactured products. In principle, each valve and each pipe is a potential point of leakage and, therefore, a potential source of toxic or explosive gas. It is highly desirable, and often a regulatory requirement, to monitor the air at petrochemical plant facilities continuously, and at multiple locations, for the presence of toxic or explosive components.

Air monitoring of facilities, such as petrochemical facilities, is ideally performed with a plurality of sampling or intake stations distributed throughout the facility. Various methods of sampling have been used in the prior art. These methods can be categorized into one of three general approaches, which will be briefly outlined below.

One prior art method is based upon sampling and analysis of the sample at multiple locations. This method usually detects pollutants soon after emission, but this method is usually impractical if monitoring must be performed at numerous locations or "stations" within the facility. Using once again a petrochemical facility as an example, it is typically desirable to monitor the air in the facility at twenty, thirty or even more monitor stations in order to obtain a representative picture of any valve, piping or equipment malfunctions. If a gas chromatography (GC) is used to analyze the captured air samples, then this method would require twenty, thirty, or even more GCs, and qualified operators for each, located throughout the facility. Such requirements would not be feasible from both an economic and an operational criteria.

In another prior art method, gas samples are captured in closed containers periodically and then transported in these closed containers to a central facility, such as a laboratory, for analysis. The use of a central laboratory is certainly more cost effective that the use of distributed analysis equipment. Time between sampling and analysis can, however, be significant. This time "lag" allows dangerous gasses to be emitted for significant time periods before they are detected, and before remedial actions can be taken.

Another prior art systems utilize remote gas intakes distributed throughout a facility, and sequentially draw gas samples through these intakes through connecting flow conduits to a multiple valve system with multiple ports. Sample from one port is sequentially selected and directed to an analysis apparatus, such as a GC, for analysis. Typically, sample gas (such as air) is only flowing from the intake and conduit connecting the selected port. Sample gas drawn into the analysis apparatus from the next selected port is not "fresh", at least at the beginning of the analysis process, in that it might have been drawn into the connecting sample intake minutes or even hours earlier. As a result, quantitative analysis will not yield a true measure of any pollutants being emitted at the location of the intake at the time of the analysis. Once again, this situation results a dangerous time lag between emission of dangerous pollutants and the detection of the pollutants. Although the time lag is usually not as great as that using previously discussed technique of capturing discrete samples in closed containers for analysis at a central laboratory, it can still lead to undetected emissions which can lead to catastrophic results.

In view of the prior art discussed above, there is a need for apparatus and methods for analyzing gas samples, and more particularly air samples, which utilizes a central analysis apparatus and still provides results without excessive lag time. This objective can be accomplished by presenting "fresh" samples from multiple, remote locations at a central location for analysis by a central analysis apparatus.

SUMMARY OF THE INVENTION

One object of the present invention is to provide a multiport valve through which gas samples, drawn from multiple and remote locations, continuously flow thereby providing fresh samples from these locations for analysis.

Another object of the invention is to provide a valving system with which gas samples can be sequentially drawn from multiple ports for analysis.

Still another object of the present invention is to provide a multiport valve from which gas from one port can be drawn for analysis while gas from other remote locations continues to flow uninterrupted thereby providing fresh sample at all time for the next sequentially selected port yielding representative analysis results with minimal time lag.

Another object of the invention is to provide a multiport valve for receiving gas samples and means for drawing sample from a selected port with reduced chance of cross contamination from gases flowing to non selected ports.

Yet another object of the present invention is to provide a multiport monitoring system wherein flow rates of gases delivered to ports of a multiport valve are equalized thereby equalizing the analysis sensitivity of gases drawn from sequentially selected ports.

Another object of the present invention is to provide a multiport valve system which is programmable, wherein the number of active ports and the sequence of sampling of these ports can be easily selected and change by programming an actuator which controls the operation of the valve.

There are other objects and applications of the present invention that will become apparent in the following disclosure.

The heart of the valving system set forth in this disclosure is a multiport valve comprising three basic components which are a valve body containing multiple inlet ports, a rotating bar and shaft assembly or "rotor" assembly which is positioned to select designated ports, and a bonnet affixed to the valve body thereby enclosing the rotating bar and defining a chamber. One port is "selected" in that sample is drawn from this port into an analysis apparatus. For purposes of discussion, it will be assumed that the valve contains 32 ports. It should be understood that fewer or more ports can be used, as will be discussed in detail in subsequent sections of this disclosure.

The multiport valve is configured so that sample gas, typically air, is directed through each port continuously, regardless of whether the port is currently selected for analysis or simply on standby waiting to be selected. This provides fresh sample at all times at all ports of the valve, where these sample gases are typically drawn from remote, multiple sample intakes spaced at various locations in a facility being monitored. A first vacuum is applied to the valve to draw sample gas to the valve through the ports not currently being analyzed, or "non selected" ports. A second vacuum, typically a vacuum supplied by an analysis apparatus such as a GC, draws gas through the selected port and into the analysis apparatus.

Port selection within the valve is accomplished by rotating the bar and shaft assembly within the valve to connect the selected port, by means of flow passages within the bar and cooperating valve shaft, to an outlet port connected to the analysis apparatus. After a predetermined sample time, the bar is then rotated to another port thereby selecting gases flowing to this port for passage to the analysis apparatus. The bar and shaft assembly is connected to a programmable actuator, which rotates the assembly at programmed time intervals and in a programmed sequence. Gases not flowing to the selected port are passed into the chamber and subsequently swept by the first vacuum source to a suitable disposal means. Gas flowing to the selected port is passed into and through the analysis apparatus. In subsequent discussion, it will be assumed that the analysis is a GC, although other analysis devices such as various types of spectrometers and hot wire analysis devices can be used. Furthermore, it will be assumed, for purposes of discussion, that the sample gases are air samples which are being analyzed by the GC for explosive components, toxic components, or both types of pollutants.

In most applications, air samples are drawn from remote locations which are not equidistant from the multiport valve and cooperating CG apparatus. In practice, the flow lines connecting intakes at these remote locations can vary in length from a few feet to distances approaching a mile. Since sample is typically drawn in all flow lines by a vacuum source at the valve assembly, flow rates into the valve ports are not expected to be equal, since the length of the feed lines can vary over orders of magnitude in length. These unequal flow rates could lead to erroneous quantitative measures of the pollutants since the GC column would normally be calibrated for a given flow rate. In order to equalize flow rates, flow meters are installed in each feed line and preferably as near as practical to the multiport valve. Each flow meter is set to yield the same flow rate in each feed line going into each valve port.

In summary, air samples are drawn into remote and distributed intakes and passed through flow lines to the multiport valve assembly. Sample gases are typically moved by the vacuum source attached to the valve chamber. The bar and shaft assembly is rotated within the valve to sequentially select a port, and gas is drawn from this port and passed to an analysis apparatus which, for purposes of discussion, is a CG. Rotation is controlled by a programmable actuator attached to the bar and shaft assembly. Non selected gas samples continuously flow into the valve chamber, and are subsequently purged from the chamber to waste. Selected samples are analyzed for pollutants in the GC, and these results are typically printed in tabular and chart form, and alternately stored in a digital memory for archival purposes and for further analysis.

BRIEF DESCRIPTION OF THE DRAWINGS

So that the manner in which the above recited features, advantages and objects of the present invention are attained call be understood in detail, more particular description of the invention, briefly summarized above, may be had by reference to the embodiments thereof which are illustrated in the appended drawings.

It is to be noted, however, that the appended drawings illustrate only typical embodiments of the invention and are therefore not to be considered limiting of its scope, for the invention may admit to other equally effective embodiments.

DETAILED DESCRIPTION OF THE PREFERRED EMBODIMENT

Figure 1:
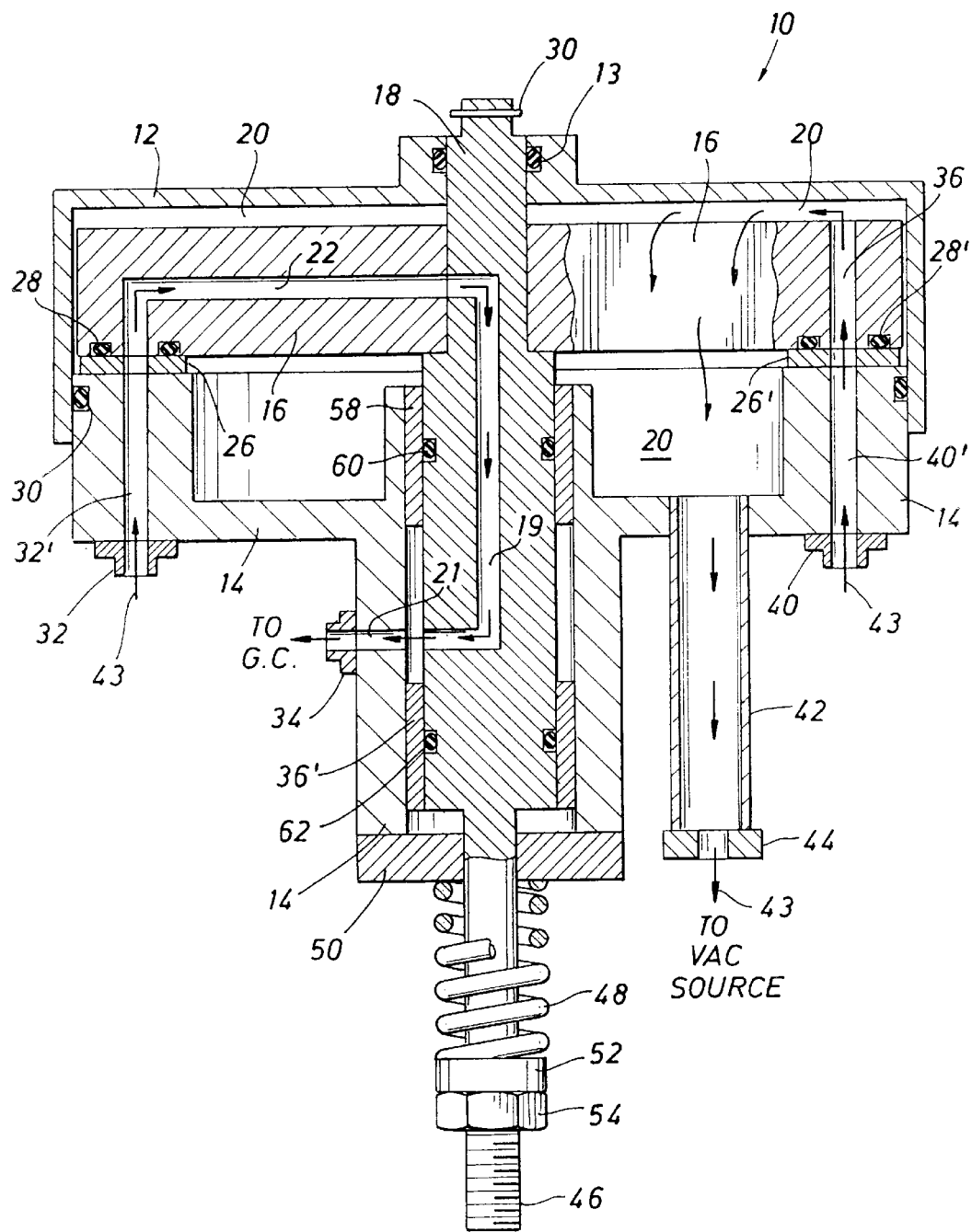
FIG. 1 is a sectional view of the multiport valve.

FIG. 1 shows a sectional view of the multiport valve 10 in the preferred embodiment. The valve comprises three main elements which are a cylindrical valve body 14, a rotating bar 16 and affixed to a shaft 18, and a cylindrical bonnet 12 which is attached to the valve body thereby enclosing the rotating bar and shaft and further defining a chamber 20. The rotating bar and shaft assembly will be referred to as a rotor assembly for brevity. The bar 16 preferably made of steel and is about 1 inch (in.)×1 in.×6 in, but other dimensions can be used as will be discussed later. The construction and even operation of the valve can perhaps be seen better by referring to both FIG. 1 and a perspective view in FIG. 2 with the bonnet 12 removed.

The valve body contains a plurality of passages 40' and a 32' which terminate at their lower ends with fittings 40 and 32, respectively, and which extending through the valve body and opening into the chamber 20. The passages 40' and 32' and fittings 40 and 32 are identical, but the numeral 32 is used to identity a single "selected" port while the numeral 40 is used to identify all other ports as will become apparent in the following paragraphs.

Referring to FIG. 1, the left side of the bar 16 contains a passage 22 which connects with a passage 19 in the shaft 18 which, in turn, connects with another passage 21 in the valve body 14. The passage 21 is terminated on the outside of the valve body with a fitting 34 thereby defining a sample outlet. Sample to be analyzed is then drawn into the selected port 32 and passes through the multiport valve 10 as shown by flow arrows 43, and exits at the sample outlet 34 where it passes to an analyzer apparatus such as a GC (see FIG. 3). The right side of the bar 16 contains a passage 36 which connects the port 40 opposite the selected port 32 directly to the chamber 20. Sample flowing through this port, as well as sample flowing through the other non selected ports 40, flows into the chamber 20 and is drawn, or "purged", from the chamber out through a waste port 42 by a vacuum source (see FIG. 3) attached at fitting 44. These samples are then disposed as waste in a manner safe to life and property. Gas flow is again illustrated by the flow arrows 43.

All sample gas from non selected ports 40, including the port opposite the selected port 32, flows into and commingles within the chamber 20. From a sample flow aspect, the right side of the bar 16 is not functionally involved. The right hand side of the bar 16 does, however, serve as a balance as the bar 16 is advanced from one selected port to the next selected port by the valve actuator.

It is of great importance to provide good seals at the bar-valve housing interface. This seal prevents gas flowing through the selected port 32 from being contaminated by gases flowing through all non selected ports 40. Proper seals are insured by partially pliable buttons 26 and 26' mounted on the rotating bar 16 at the passage openings 22 and 36, respectively, as shown in FIG. 1. The buttons are preferably fabricated from Teflon® (manufactured by DuPont) although other resilient materials can be used. The buttons 26 are also preferably disk shaped with a centered opening, and have the lower surfaces lapped to obtain maximum seal with the lapped, interfacing upper surfaces of the valve housing 14 in the vicinity of each port passage. The bar 16 is preferably welded to the shaft 18. This can introduce some dimensional tolerance buildup at the bar-port interfaces due to warping. To insure good seals even with this tolerance buildup, O-ring assemblies 28 and 28' on the bar 16 are used to back the Teflon® buttons 26 and 26', respectively. This allows the Teflon® buttons to adjust and properly seat against the valve body 14, even if the bar 16 is slightly warped at the weld to the shaft 18.

Tension between the Teflon® button seals 26, 26' on the rotating bar 16 and the corresponding port passages 32,40 in the valve body 14 is adjustable. Again referring to FIG. 1, the lower end of the rotating shaft 18 of the rotor assembly passes through the lower portion of the valve body 14, and through a valve mounting plate 50, and then terminates at a threaded rod 16. The threaded rod 46 is surrounded by a spring 48. A thrust bearing sleeve 52 terminates the lower end of the spring 48 and is contained by a hex nut 54 on the threaded rod 16. The degree of compression of the spring 48 is a function of the position of the nut 54 on the rod. Tension at the Teflon® button seals can, therefore, be adjusted by rotating the hex nut.

The shaft 18 contacts the valve housing 14 at an upper bearing 58 and a lower bearing 36' as illustrated in FIG. 1. Upper and lower O-ring assemblies 60 and 62 provide seals to assure that gas flowing through the passages 19 and 21, and subsequently to the GC, is not contaminated by other non selected flowing gas in the chamber 20. The chance of cross contamination is further reduced by applying a vacuum at the fitting 44 which is greater than vacuum applied to the sample outlet 34. Stated another way, the pressure differential between passages leading from the selected port and the chamber is always positive. With this arrangement, any leakage at the O-ring seals 60 or 62 will result in a flow of selected sample gas into the chamber 20 rather than a flow of non selected gas in the chamber 20 into the passages 19 and 21 and to the GC.

Attention is next directed to the bonnet 12 as shown in FIG. 1. As stated previously, the bonnet 12 along with the valve body 14 defines the chamber 20 to which a vacuum source is applied at the fitting 44. The bonnet must, therefore, be properly sealed to the valve body. This is accomplished with an O-ring assembly 13 which seals the side of the bonnet 12 to the side of the valve body 14. The bonnet is sealed against the rotating shaft 18 by the O-ring assembly.

As mentioned previously, the number of sample ports 40 can be varied. A typical number is thirty two. The maximum number of ports is, however, governed to some extent by the circumference of the valve body 14. As an example, if 32 ports are used with a valve body of about 21 in. in circumference (6 in. diameter), and it is required that standard ¼ in.×⁷⁄₁₆–20 SAE male connectors be used as input fittings, it would not be geometrically possible to mount all fittings on the lower side of the valve body 14 as shown in FIG. 1. As an alternate, the input fittings can be "staggered", and be alternately mounted on the bottom and the side of the valve body 14 with an appropriate rerouting of the passages 32', 40' for the side mounted fittings. As a second alternate, the valve body 14 and rotating bar 16 could simply be made larger allowing all fittings, and even additional fittings for additional ports, to be aligned on a single surface (top or side) of the valve body. If fewer ports are needed, the unused ports can simply be plugged and the valve actuator is programmed to bypass these ports.

Figure 2:
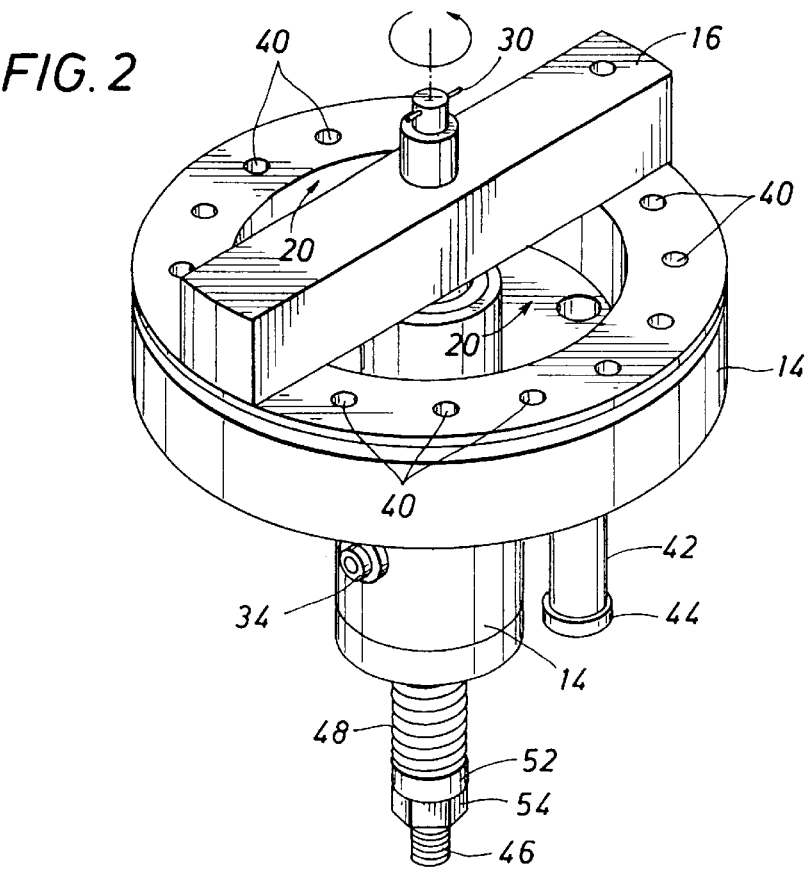
FIG. 2 is a perspective view of the multiport valve with the bonnet removed.
Figure 3:
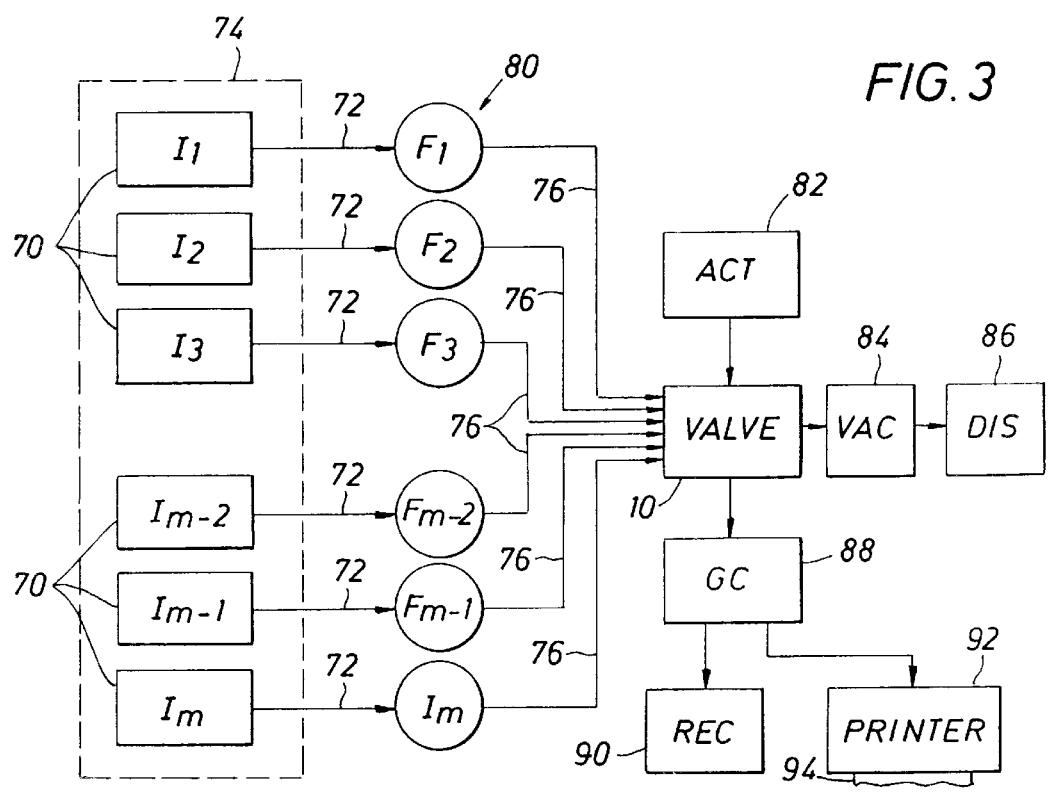
FIG. 3 is a functional diagram of the multiport valve and sampling system.

The valve actuator 82 used to rotate, position and advance the bar 16 within the multiport valve assembly 10 is shown in the functional diagram in FIG. 3. A suitable, programmable valve actuator is manufactured by Valco Instruments Inc. of Houston, Tex. The Actuator grasps top end of the shaft 18 with a cup fitting (not shown) employing two "U" brackets which engage a pin 30 through the upper end of the shaft 18 as shown in FIGS. 1 and 2. The actuator can be programmed to move the bar 16 sequentially from one port to the next adjacent port. Alternately, the actuator can be programmed to skip ports, and to rotate the shaft and attached bar counter clockwise as shown in FIG. 2, or clockwise.

A functional diagram of the entire multiport valve system and supporting equipment is shown in FIG. 3. The valve comprises "n" ports. A typical value for n is 32. Intakes $I_1$, $I_2$, $I_2$, $I_n$ are designated by the numeral 70 and are located remotely at a facility being monitored, which is indicated conceptually with a broken line box 74. Each intake $I_j$ (j=1, ..., n) draws gas, typically air, from its surrounding location and is connected by means of a dedicated flow line 72 to a corresponding flow meter $F_j$ (j=1, ..., n). The flow meters are identified as a group by the numeral 80. Output from each flow meter is directed to an inlet port 40 (see FIGS. 1 and 2) of the multiport valve 10, or to inlet 32 if that particular inlet is the selected inlet at that time in the sampling procedure. A port is selected when the programmable actuator 82 positions the bar 16 over this port, as previously discussed and as also illustrated in FIG. 1. A vacuum source 84 assures that sample gas from all other intakes 70 continues to flow to the vent port thereby assuring that "fresh" sample will be available at all ports when they are selected. The vacuum source, which is preferably an eductor vortex device, purges all non selected gas sample, which flows through all non selected ports and into the chamber 20, to a suitable disposal means 86.

The lines 72 are typically unequal in length as discussed previously, since the intakes $I_j$ are distributed at varying locations throughout the facility 74 being monitored. The lengths of the lines 72 can, in fact, vary by orders of magnitude. The flow meters 80 are set to yield a constant flow rate to each port of the multiport valve 10 through flow lines 76, thereby assuring that flow rates delivered from the valve to the GC analysis apparatus 88 is constant. This insures that analytical concentrations of pollutants emitted by the GC column are accurate in that they are commensurate with the flow rate calibration of the GC. Analysis results are printed in tabular or chart form by a printer 92 and preferably output as a hard copy 94. Alternately, analysis results are stored by a recording device 90, such as a magnetic disk recorder, for subsequent analysis and archiving.

Pressure of gas at the inlet ports of the valve is typically about 2 atmospheres or lower when the valve 10 is in the operative position. At these pressures, it has been determined that the previously described sealing structure between the rotating bar and the port passages within the valve body do not leak.

It should be noted that the flow meters $F_j$ are not needed to operate the multiport valve 10, and are not needed to obtain results from the analysis apparatus 88. They are however, used to yield improved analysis results from a flow rate dependent analysis apparatus such as a GC.

In summary, intakes 70 are positioned throughout various critical locations in a facility 74, such as a petrochemical manufacturing plant, where toxic or explosive or noxious gases might accumulate. Each intake is connected to a remote multiport valve by a dedicated flow line 72. Gas in drawn from the intake to all inlet ports of the valve 10, with the exception of the currently selected port, by the vacuum source 84. Sample gas is drawn through the selected port by a second vacuum source cooperating with the analysis apparatus 88, such as a source to move gas through a GC column. Gas drawn through the selected port from a corresponding intake 70 is then analyzed giving the concentration of pollutants at the position of that intake. Non selected gas samples are purged to waste.

While the foregoing is directed to the preferred embodiments of the invention, the scope of the invention is determined by the claims that follow.

What is claimed is:

1. A gas monitoring system comprising:
   (a) a multiport valve comprising a rotor assembly which is confined to move within a defined plane;
   (b) a plurality of intakes remote from said multiport valve, wherein each said intake is connected to a specific inlet port of said valve by means of a dedicated flow line;
   (c) a programmable actuator to operate said valve to select gas from one said intake for sampling, wherein
      (i) said selected gas and non selected gas flows continuously through said valve,
      (ii) said selected gas is isolated by a gas tight seal from said non selected gas,
      (iii) a positive pressure differential exists between said selected gas and said non selected gas within said valve, and
      (iv) non selected gas is purged from said valve to waste.

2. The system of claim 1 further comprising a plurality of flow meters, wherein:
   (a) one said flow meter is installed in each said dedicated flow line; and
   (b) the flow rate through each said flow meter is set so that flow rates of said selected gas and said non selected gases into said multiport valve are controlled to selected values.

3. The system of claim 1 further including a vortex eductor connected to said multiport valve to purge said non selected gas to waste.

4. The system of claim 1 further comprising an analysis apparatus for said selected gas sample.

5. The system of claim 4 further comprising a data output means for outputting the results of analysis of said selected gas by said analysis apparatus.

6. The system of claim 1 wherein said multiport valve comprises:
   (a) a valve body comprising at least two said inlet ports, and each said inlet port has sample gas supplied by said dedicated flow line connected to the inlet port;
   (b) a bonnet attached to said valve body thereby defining a chamber;
   (c) said rotor assembly within said chamber, wherein a rotor opening is positioned at a selected inlet port to obtain from said selected gas a selected sample gas; and
   (d) flow passages within said rotor assembly and said valve body through which said selected gas flows to a valve outlet; wherein
      (i) said sample gas flows continuously through each of said at least two inlet ports,
      (ii) said selected sample gas is directed from said valve outlet to an analysis apparatus, and
      (iii) said non selected gas flows into said chamber from and is subsequently purged as waste.

7. The system of claim 1 wherein differential pressure between said flow passages and said chamber of said multiport valve is positive.

8. The system of claim 1 wherein said multiport valve further comprises a waste port connected to said chamber and through which said non selected sample gas is drawn.

9. The system of claim 1 wherein said multiport valve further comprises a pliable button, wherein an interface between said rotor and said inlet port is sealed by said pliable button.

10. The system of claim 9 wherein said multiport valve further comprises an O-ring assembly within said rotor and backing said pliable button, wherein said O-ring assembly enhances said seal.

11. The system of claim 9 wherein said pliable button in said multiport valve is resilient.

12. The system of claim 9 wherein said multiport valve further comprises:
   (a) an elongated extension of said rotor extending through said valve body;
   (b) a threaded rod attached to the end of said extension;
   (c) a spring acting on said threaded rod and resiliently bearing at one end on a mounting plate and bearing at a second end on a thrust bearing; and
   (d) a nut contacting said thrust bearing, wherein tension at said spring is adjusted by turning said nut.

13. The system of claim 1 wherein said rotor assembly in said multiport valve is moved by said programmable actuator so that said rotor moves an opening to a selected inlet port.

14. The system of claim 13 wherein said rotor of said multiport valve is moved sequentially to adjacent ports within said valve body by said programmable actuator.

15. The system of claim 1 wherein said rotor of said multiport valve comprises:
   (a) a central rotatable shaft; and
   (b) a transverse, two ended bar.

16. A method for selecting a gas for analysis from a plurality of gases, the method comprising the steps of;
   (a) providing a valve comprising a valve body and a bonnet which cooperate to define a chamber, wherein said valve body comprises at least two inlet ports, each to which sample gas is supplied;
   (b) continuously flowing gas to each said ports;
   (c) rotating a rotatable rotor assembly and confining motion to a defined plane within said chamber and positioning an inlet opening of said rotor at a selected inlet port, and forming a gas tight seal between said inlet port and said selected inlet, and thereby directing selected gas from said selected inlet port to an outlet port for analysis; and (d) flowing non selected gas into said chamber, and subsequently purging said non selected gas from said chamber to waste.

17. The method of claim 16 including the additional steps of;
   (a) flowing said selected gas from said selected inlet port to said outlet port through passages within said rotor assembly; and
   (b) maintaining a positive pressure differential between said selected gas in passages and non selected gas in said chamber.

18. The method of claim 17 including the additional step of equalizing the flow rate of gas into each of said at least two inlet ports.

19. The method of claim 17 including the additional steps of:
   (a) providing a programmable actuator; and
   (b) rotating said rotor assembly with said programmable actuator a predetermined time intervals and to adjacent inlet ports in said valve body.

20. The method of claim 17 including the additional steps of:
   (a) providing an analysis apparatus; and
   (b) directing said selected gas from said outlet port and into said analysis apparatus for analysis.

21. The method of claim 17 including the additional steps of:
   (a) providing a vacuum source;
   (b) connecting said vacuum source to said chamber; and
   (c) purging said non selected gas from said chamber by means of said vacuum source.

* * * * *